US006656922B2

(12) United States Patent
Byun et al.

(10) Patent No.: US 6,656,922 B2
(45) Date of Patent: Dec. 2, 2003

(54) ORAL DELIVERY OF MACROMOLECULES

(75) Inventors: Youngro Byun, Gwangju (KR); Yong-Kyu Lee, Gwangju (KR)

(73) Assignee: Mediplex Corporation, Korea, Seoul (KR)

( * ) Notice: Subject to any disclaimer, the term of this patent is extended or adjusted under 35 U.S.C. 154(b) by 0 days.

(21) Appl. No.: 09/845,827

(22) Filed: Apr. 30, 2001

(65) Prior Publication Data
US 2002/0010153 A1 Jan. 24, 2002

Related U.S. Application Data

(63) Continuation-in-part of application No. 09/300,173, filed on Apr. 27, 1999, now Pat. No. 6,245,753.

(30) Foreign Application Priority Data

May 28, 1998 (KR) .............................................. 98-19469

(51) Int. Cl.$^7$ ............................................ A61K 31/727
(52) U.S. Cl. ................................ 514/56; 514/3; 514/12; 514/54; 514/57; 530/303; 530/307; 536/17.5; 536/21; 536/56; 536/92; 536/95; 536/122; 536/123.1; 604/890.1; 604/891.1; 606/228; 606/231
(58) Field of Search .............................. 514/54, 56, 57; 536/21, 17.5, 56, 92, 95, 122, 123.1; 606/228, 231; 604/890.1, 891.1

(56) References Cited

U.S. PATENT DOCUMENTS

| 4,857,602 A | 8/1989 | Casey et al. ................. 525/408 |
| 5,840,387 A | 11/1998 | Berlowitz-Tarrant et al. .... 428/36.91 |
| 5,855,618 A | 1/1999 | Patnaik et al. ................. 623/11 |

OTHER PUBLICATIONS

A. Leone–Bay, et al.; 4–[4–(2–Hydroxybenzoyl)amino]phenyl butyric Acid as a Novel Oral Delivery Agent for Recombinant Human Growth Hormone, 39 J. Med. Chem. 2571–2578 (1996).
R. Altman, et al.; Oral Anticoagulant Treatment with and without Aspirin, 74(1) F.K. Schattauer Verlagsgesellschaft mbH (Stuttgart) 506–510 (1995).
B. Koefoed, et al., Effect of Fixed Minidose Warfarin, Conventional Dose Warfarin and Aspirin on INR and Prothrombin Fragment 1+2 in Patents with Atrial Fibrillation, 77 (5) F.K. Schattauer Verlagsgesellschaft mbH (Stuttgart) 845–848 (1997).
P. Klement, et al., Hirudin causes more bleeding than heparin in a rabbit ear bleeding model, 132 J. Lab Clin Med 181–185 (1998).
R. Hull, et al.; Hirudin versus heparin and low–molecular–weight heparin: And the winner is . . . , 132 J. Lab Clin Med 151–174 (1998).

G.E. Raskob, Msc. Low molecular weight heparin, heparin, and warfarin, 2 Current Opinion in Hematology 372–379 (1995).
L. Wallentin, Unstable coronary artery disease—need for long term antithrombotic treatment, Aspirin alone is not sufficient, I would associate anticoagulant, 33 Cardiovascular Research 292–294 (1997).
S. Milstein, et al., Partially unfolded proteins efficiently penetrate cell membranes—implications for oral drug delivery; 53 Journal of Controlled Release 259–267 (1998).
A. Leone–Bay, et al, The evolution of an oral heparin dosing solution, 22(8) Drugs of the Future 885–891 (1997).
A. Leone–Bay, et al., Oral Delivery of Sodium Cromolyn: Preliminary Studies In Vivo and In Vitro, 13(2) Pharmaceutical Research 222–226 (1995).
A. Leone–Bay, et al., N–Acylated α–Amino Acids as Novel Oral Delivery Agents for Proteins, 38 J. Med. Chem. 4263–4269 (1995).
E. Windsor & G. Cronheim, Gastro–Intestinal Absorption of Heparin and Synthetic Heparinoids, 190 Nature 263–264 (1961).
A. Leone–Bay, et al., Acylated non–α–amino acids as novel agents for the oral delivery of heparin sodium, USP, 50 Journal of Controlled Release 41–49 (1998).
D. Brayden, et al., Heparin Absorption Across the Intestine: Effects of Sodium $n$–[8–(2–Hydroxybenzoyl) Amino] Capyrlate in Rat In Situ Intestinal Instillations and in Caco–2 Monolayers, 14(12) Pharmaceutical Research 1772–1779 (1997).
A. Leone–Bay, et al., Synthesis and Evaluation of Compounds That Facilitate the Gastrointestinal Absorption of Heparin, 41 J. Med. Chem 1163–1171, (1998).
A. Leone–Bay, et al., Microsphere Formation in a Series of Derivatized α–Amino Acids: Properties, Molecular Modeling, and Oral Delivery of Salmon Calcitonin, 38 J. Med. Chem 4257–4262 (1995).
Y.–K. Lee et al., Preparation of Slightly Hydrophobic Heparin Derivatives which Can Be Used for Solvent Casting in Polymeric Formulation, 92 Thrombosis Res. 149–156 (1998).

(List continued on next page.)

*Primary Examiner*—Peter O'Sullivan
(74) *Attorney, Agent, or Firm*—Clayton, Howarth & Cannon, P.C.

(57) ABSTRACT

Polysaccharides, which are widely used as an anticoagulation drugs, especially heparin, are clinically administered only by intravenous or subcutaneous injection because of their strong hydrophilicity and high negative charge. Amphiphilic heparin derivatives were synthesized by conjugation to bile acids, sterols, and alkanoic acids, respectively. These heparin derivatives were slightly hydrophobic, exhibited good solubility in water, and have high anticoagulation activity. These slightly hydrophobic heparin derivatives are efficiently absorbed in the gastrointestinal tract and can be used in oral dosage forms. Methods of using these amphiphilic heparin derivatives and similarly modified macromolecules for oral administration are also disclosed.

22 Claims, 6 Drawing Sheets

OTHER PUBLICATIONS

Y.–K. Lee et al., Oral Delivery of New Heparin Derivatives in Rats, 17 Pharma. Res. 1259–1264 (2000).

G.J. Russell–Jones, Carrier–mediated Transport, Oral Drug Delivery, in 1 Controlled Drug Delivery 173–183 (E. Mathiowitz ed. 1999).

P.W. Swaan et al., Enhanced Transepithelial Transport of Peptides by Conjugation to Cholic Acid, 8 Bioconjugate Chem. 520–525 (1997).

Diancourt et al. Journal of Bioactive and Compatible Polymers Jul. 1996, 11(3), 203–218.

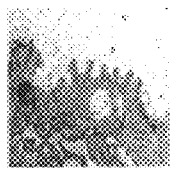 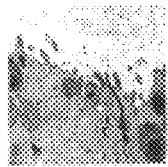 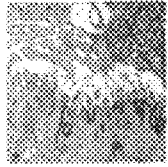 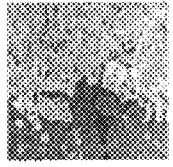
FIG. 6A  FIG. 6B  FIG. 6C  FIG. 6D
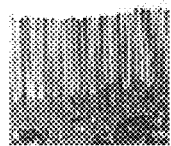 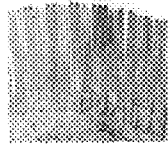  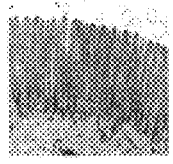
FIG. 6E  FIG. 6F  FIG. 6G  FIG. 6H
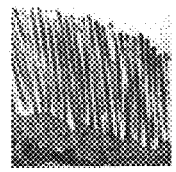 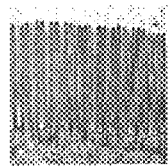 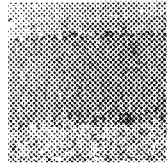 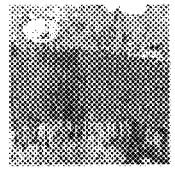
FIG. 6I  FIG. 6J  FIG. 6K  FIG. 6L
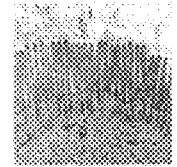 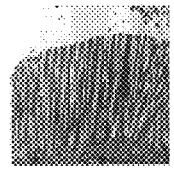 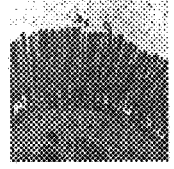 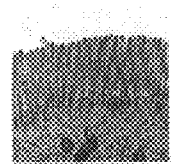
FIG. 6M  FIG. 6N  FIG. 6O  FIG. 6P

ORAL DELIVERY OF MACROMOLECULES

CROSS-REFERENCE TO RELATED APPLICATIONS

This application is a continuation-in-part of U.S. Ser. No. 09/300,173, filed Apr. 27, 1999, now U.S. Pat. No. 6,245,753, which is hereby incorporated herein by reference, which claims priority to Korean Pat. Application No. 19469, filed May 28, 1998.

STATEMENT REGARDING FEDERALLY SPONSORED RESEARCH OR DEVELOPMENT

Not applicable.

BACKGROUND OF THE INVENTION

This invention relates to derivatives of macromolecules, including polysaccharide derivatives, having increased hydrophobicity as compared to the unmodified macromolecules or polysaccharides. More particularly, the invention relates to oral delivery and absorption of hydrophobized macromolecules and amphiphilic polysaccharide derivatives, such as amphiphilic heparin derivatives, wherein the bioactivity of the macromolecule or polysaccharide is preserved. In preferred embodiments of the invention, the hydrophobized macromolecules and amphiphilic polysaccharide derivatives have a molecular weight of greater than 1000, yet are absorbed after oral administration.

Heparin is a polysaccharide composed of sulfated D-glucosamine and D-glucuronic acid residues. Due to its numerous ionizable sulfate groups, heparin possesses a strong electronegative charge. It is also a relatively strong acid that readily forms water-soluble salts, e.g. heparin sodium. It is found in mast cells and can be extracted from many body organs, particularly those with abundant mast cells. The liver and lungs are especially rich in heparin. The circulating blood contains no heparin except after profound disruption of mast cells. Heparin has many physiological roles, such as blood anticoagulation, inhibition of smooth muscle cell proliferation, and others. In particular, heparin is a potent anticoagulant agent that interacts strongly with antithrombin III (ATIII) to prevent the formation of fibrin clots. Heparin is one of the most potent anticoagulants used for treatment and prevention of deep vein thrombosis and pulmonary embolism. In vivo, however, applications of heparin are very limited. Because of its hydrophilicity and high negative charge, heparin is not absorbed efficiently from the GI tract, nasal or buccal mucosal layers, and the like. Therefore, the only routes of administration used clinically are intravenous and subcutaneous injections. Moreover, since heparin is soluble in relatively few solvents, it is hard to use for coating surfaces of medical devices or in delivery systems.

To improve the properties of heparin, R. J. Linhardt et al., 83 J. Pharm. Sci. 1034–1039 (1994), coupled lauryl ($C_{12}$) and stearyl ($C_{18}$) groups to single heparin chains, resulting in a derivatized heparin having increased hydrophobicity but with low anticoagulation activity. This result demonstrated that coupling a small linear aliphatic chain to heparin was ineffective in enhancing the hydrophobicity of heparin while preserving activity. Thus, known heparin derivatives have been ineffective in preserving anticoagulation activity.

T. M. Rivera et al., Oral Delivery of Heparin in Combination with Sodium N-[8-(2-Hydroxybenzolyl)amino]caprylate: Pharmacological Considerations, 14 Pharm. Res. 1830–1834 (1997), disclosed the possibility of oral delivery of heparin using heparin mixed with sodium N-[8-(2-hydroxybenzolyl)amino]caprylate. M. Dryjski et al., Investigations on Plasma Activity of Low Molecular Weight Heparin after Intravenous and Oral Administrations, 28 Br. J. Clin. Pharma. 188–192 (1989), described the possibility of oral absorption of low molecular weight heparin using enhancers.

It is generally recognized that molecules having a molecular weight greater than 1000 are poorly absorbed in the gastrointestinal (GI) tract after oral administration. For example, J. G. Russell-Jones, Carrier-mediated Transport, Oral Drug Delivery, in 1 Encyclopedia of Controlled Drug Delivery 173, 175 (Edith Mathiowitz ed. 1999), stated that the work of W. Kramer et al., 269 J. Biol. Chem. 10621–10627 (1994), suggested that the maximal size of a peptide that could be transported via the bile acid transporter was four amino acids, or about 600 Da. As another example, P. W. Swaan et al., Enhanced Transepithelial Transport of Peptides by Conjugation to Cholic Acid, 8 Bioconjugate Chemistry 520–525 (1997), reported that bile acid conjugates with up to 6 amino acids (i.e., about 900 Da) showed affinity for the intestinal bile acid transporter, but the only 6-amino-acid bile acid conjugate tested was not transported by the bile acid carrier.

In view of the foregoing, it will be appreciated that development of a method for obtaining absorption of macromolecules having a molecular weight greater than 1000 after oral administration would be a significant advancement in the art. It will also be appreciated that development of a method for obtaining absorption of hydrophobized or amphiphilic heparin derivatives after oral administration would be another significant advancement in the art.

BRIEF SUMMARY OF THE INVENTION

It is an object of the present invention to provide a method for obtaining absorption of molecules having a molecular weight greater than 1000 after oral administration.

It is also an object of the invention to provide a method for obtaining blood anticoagulation by oral administration of amphiphilic heparin derivatives.

It is still another object of the invention to provide heparin derivatives that can be absorbed from the GI tract, thereby facilitating oral delivery for preventing blood coagulation.

It is yet another object of the invention to provide heparin derivatives comprising heparin coupled with a bile acid, such as deoxycholic acid or glycocholic acid, or a hydrophobic agent, such as cholesterol, or an alkanoic acid.

These and other objects can be addressed by providing a method of treating a patient in need of anticoagulation therapy comprising orally administering an effective amount of a composition comprising heparin covalently bonded to a hydrophobic agent selected from the group consisting of bile acids, sterols, and alkanoic acids, and mixtures thereof. The composition can also include a pharmaceutically acceptable carrier.

In one preferred embodiment of the invention the hydrophobic agent is a bile acid selected from the group consisting of cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and mixtures thereof, and the like.

In another preferred embodiment of the invention, the hydrophobic agent is a sterol selected from the group consisting of cholestanol, coprostanol, cholesterol, epicholesterol, ergosterol, ergocalciferol, and mixtures thereof, and the like.

In still another preferred embodiment of the invention, the hydrophobic agent is an alkanoic acid comprising about 4 to 20 carbon atoms. Preferred alkanoic acids include butyric acid, valeric acid, caproic acid, caprylic acid, capric acid, lauric acid, myristic acid, palmitic acid, stearic acid, and mixtures thereof, and the like.

Preferably, the heparin comprises a molecular weight of at least about 3000, and more preferably at least about 6000. In certain preferred embodiments, the heparin comprises a molecular weight less than about 12,000.

Another preferred embodiment of the invention comprises a method for enhancing oral administration of a macromolecular agent comprising:

(a) conjugating the macromolecular agent to a hydrophobic agent selected from the group consisting of bile acids, sterols, alkanoic acids, and mixtures thereof, and the like to result in a hydrophobized macromolecular agent; and (b) orally administering an effective amount of the hydrophobized macromolecular agent to a patient in need thereof.

Preferably, the macromolecular agent is a member selected from the group consisting of heparin, heparan sulfate, sulfonyl polysaccharide, heparinoids, polysaccharide derivatives, and mixtures thereof, and the like. In another preferred embodiment of the invention, the macromolecular agent is a peptide, such as insulin or calcitonin.

BRIEF DESCRIPTION OF THE SEVERAL VIEWS OF THE DRAWINGS

FIGS. 5A–D show cross sections of the stomach after 0, 1, 2, and 3 hours, respectively; FIGS. 5M–P show cross sections of the ileum after 0, 1, 2, and 3 hours, respectively; the original magnification was 100× in all FIGS. 5A–P.

FIGS. 6A–P show electron micrographs of membrane or microvilli in gastrointestinal tissues isolated from rats after oral administration of 100 mg/kg of heparin-DOCA conjugate: FIGS. 6A–D show cross sections of the of the stomach after 0, 1, 2, and 3 hours, respectively; FIGS. 6E–H show cross sections of the duodenum after 0, 1, 2, and 3 hours, respectively; FIGS. 6I–L show cross sections of the jejunum after 0, 1, 2, and 3 hours, respectively; and FIGS. 6M–P show cross sections of the ileum after 0, 1, 2, and 3 hours, respectively; the original magnification was 25,000× in all of FIGS. 6A–P.

DETAILED DESCRIPTION

Figure 1:
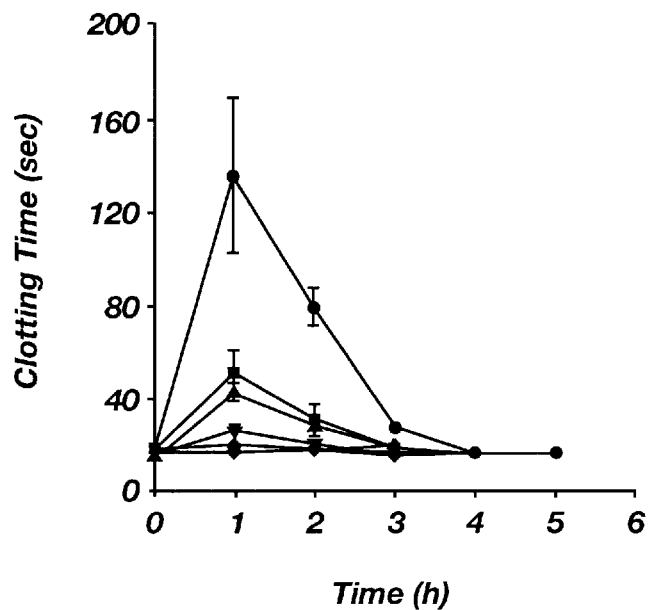
FIG. 1 shows clotting time profiles as measured by aPTT assay of heparin-DOCA conjugate after oral administration in rats: ♦—100 mg/kg raw heparin (control), ◊—physical mixture of heparin (200 mg/kg) and DOCA (200 mg/kg); ▼—50 mg/kg heparin-DOCA conjugate, ▲—80 mg/kg heparin-DOCA conjugate, ■—100 mg/kg heparin-DOCA conjugate, and ●—200 mg/kg heparin-DOCA conjugate; data are plotted as mean±SD, n=9.

Before the present methods for obtaining absorption of orally delivered hydrophobized macromolecules and amphiphilic polysaccharide compositions are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise.

Thus, for example, reference to "a bile acid" includes a mixture of two or more of such bile acids, reference to "an alkanoic acid" includes reference to one or more of such alkanoic acids, and reference to "a sterol" includes reference to a mixture of two or more sterols.

In describing and claiming the present invention, the following terminology will be used in accordance with the definitions set out below.

As used herein, "bile acids" means natural and synthetic derivatives of the steroid, cholanic acid, including, without limitation, cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and mixtures thereof, and the like.

As used herein, "sterols" means alcohols structurally related to the steroids including, without limitation, cholestanol, coprostanol, cholesterol, epicholesterol, ergosterol, ergocalciferol, and mixtures thereof, and the like.

As used herein, "alkanoic acids" means saturated fatty acids of about 4 to 20 carbon atoms. Illustrative alkanoic acids include, without limitation, butyric acid, valeric acid, caproic acid, caprylic acid, capric acid, lauric acid, myristic acid, palmitic acid, stearic acid, and mixtures thereof, and the like.

As used herein, "hydrophobic heparin derivative" and "amphiphilic heparin derivative" are used interchangeably. Heparin is a very hydrophilic material. Increasing the hydrophobicity of heparin by bonding a hydrophobic agent thereto results in what is termed herein an amphiphilic heparin derivative or hydrophobic heparin derivative. Either term is proper because the heparin derivative has increased hydrophobicity as compared to native heparin and the heparin derivative has a hydrophilic portion and a hydrophobic portion and is, thus, amphiphilic.

As used herein, "aPTT" means activated partial thromboplastin time, and "FXa" means factor Xa.

As used herein, "DOCA" means deoxycholic acid, and "heparin-DOCA" means a conjugate of heparin and deoxycholic acid.

As used herein, "macromolecule" means polypeptide, polysaccharide, and nucleic acid polymers with a molecular weight typically greater than 1000.

As used herein, "peptide" means peptides of any length and includes proteins. The terms "polypeptide" and "oligopeptide" are used herein without any particular intended size limitation, unless a particular size is otherwise stated. Typical of peptides that can be utilized are those selected from group consisting of oxytocin, vasopressin, adrenocorticotrophic hormone, epidermal growth factor, prolactin, luliberin or luteinising hormone releasing hormone, growth hormone, growth hormone releasing factor, insulin, somatostatin, glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, gramicidines, and synthetic analogues, modifications and pharmacologically active fragments thereof, monoclonal antibodies and soluble vaccines. The only limitation to the peptide or protein drug which may be utilized is one of functionality.

As used herein, "effective amount" means an amount of a pharmacologically active agent that is nontoxic but sufficient to provide the desired local or systemic effect and performance at a reasonable benefit/risk ratio attending any medical treatment. Thus, for example, an effective amount of a heparin-DOCA conjugate is an amount sufficient to provide a selected level of anticoagulation activity.

It is well known that heparin is used as an antithrombogenic agent to prevent blood coagulation. Heparin is highly hydrophilic because of a high density of negative charges such as are provided by sulfonic and carboxylic groups. Due to this hydrophilicity, heparin is usually administered by intravenous or subcutaneous injection. Heparin derivatives with slightly hydrophobic properties or amphiphilic properties and with high bioactivity are described herein. Hydrophobic agents, such as bile acids, e.g. deoxycholic acid (DOCA); sterols, e.g. cholesterol; and alkanoic acids, e.g. lauric acid and palmitic acid, were coupled to heparin. Both deoxycholic acid and cholesterol are non-toxic since they are naturally occurring compounds found in the body. The amine groups of heparin were coupled with carboxyl groups of the hydrophobic agents. The end carboxylic groups in DOCA, lauric acid, and palmitic acid were used directly for the coupling reaction, while the hydroxy group of cholesterol was activated by reaction with chloroacetic acid before coupling. It was determined that conjugating such hydrophobic moieties to the amine groups of heparin had little or no effect on heparin bioactivity. The coupling between heparin and hydrophobic agents was confirmed by detecting the resulting amide bond by FT-IR and $^{13}$C-NMR analysis.

The yield of the coupling reaction was about 70 to 80% and was not significantly changed by changing the hydrophobic agents or feed molar ratios. In the case of the heparin-DOCA conjugate, as the feed ratio was increased, the amount of DOCA in the conjugate was also increased. The weight % of DOCA in heparin-DOCA was 24% when the feed molar ratio of heparin to DOCA was 1:200. This molar ratio was very high compared to the ratio of amine groups in heparin to DOCA. Therefore, this feed ratio is estimated as an excess amount of DOCA.

The hydrophobic heparin derivatives according to the present invention would have many medical applications. For example, the hydrophobic heparin can be administered orally. The oral administration of heparin can greatly extend the usage of heparin as an oral anti-coagulant drug. The heparin derivative is formulated with a pharmaceutically acceptable carrier such as is well known in the art. By way of further example, hydrophobic heparin derivatives can be used as a coating material for medical devices such as catheters, cardiopulmonary bypass circuits, heart lung oxygenators, kidney dialyzers, stent or balloon coating for preventing restenosis, and the like. The hydrophobic heparin derivative is typically mixed with a carrier, and then coated on the surface of the medical device by a film casting technique such as is well known in the art.

After modification, heparin-hydrophobic agents were also found to have a tendency in fast protein liquid chromatography (FPLC®) to exhibit hydrophobic interactions with hydrophobic media, as shown by chromatography on Phenyl Sepharose® (eluting in ammonium sulfate buffer rather than phosphate buffer). These heparin derivatives showed enhanced binding affinity when compared to unmodified heparin. The increased interaction of modified heparin derivatives with Phenyl Sepharose® is attributable to its enhanced hydrophobicity, the result of the hydrophobic functional groups present. These results suggest hydrophobic heparin can be obtained by conjugating a bile acid, sterol, or alkanoic acid to heparin. In solubility tests, polar solvents or organic solvents were suitable to dissolve the heparin-hydrophobic agent conjugates.

For example, the heparin-deoxycholic acid conjugate showed good solubility in 65% acetone solution (35% water). Finally, it was determined that bioactivity of modified heparin derivatives was not appreciably influenced by conjugation with hydrophobic agents. The role of a hydrophobic agent conjugated to heparin was studied with respect to two biological activities of heparin as determined by anticoagulation and factor Xa assays. Although hydrophobicity is associated with a somewhat reduced anticoagulant activity and antifactor Xa activity, the decrease of bioactivity was not considered serious. These results indicate that blocking the amine groups of heparin had little effect on its bioactivity. The bioactivity of heparin in heparin-hydrophobic agent conjugates exhibited a progressive reduction, however, when the amount of hydrophobic agent in the conjugate exceeded 20 wt. %. At less than 20 wt. % of hydrophobic agent in the conjugates, the bioactivity of the conjugates was greater than 80% of the bioactivity of unmodified heparin. It is suggested that 80% of bioactivity in hydrophobic heparin is enough to support bioactivity in medical applications.

EXAMPLE 1

Synthesis of Heparin-DOCA Conjugates. Five ml of N-hydroxylsuccinimide (HOSU, 92 mg/5 ml) in dimethylformamide (DMF) was mixed with 5 ml of dicyclohexylcarbodiimide (DCC) (165 mg/5 ml) in DMF, followed by adding 5 ml of DOCA (196 mg/5 ml) in DMF. The mole ratio of DOCA, HOSu, and DCC was 1:1.6:1.6. The concentrations of HOSu and DCC were slightly higher than that of DOCA to activate DOCA completely. The resulting solution was reacted for 5 hours at room temperature under vacuum, and then the byproduct dicyclohexylurea (DCU), which precipitated during the reaction, was removed. The unreacted DCC was removed by adding a drop of distilled water and filtering. The remaining HOSu was also removed by adding 15 ml of distilled water. The activated DOCA was precipitated and then lyophilized. The activated DOCA was then dissolved in DMF and reacted with heparin for 4 hours at room temperature. The amounts of heparin used in such reactions ranged from 40 to 400 mg. After reaction, there were two types of products: a water soluble product and a water-insoluble product. These products were separated by filtration through a 0.45 µm membrane filter, and the water-insoluble product (i.e., activated DOCA) was dried in a vacuum oven. The water-soluble product (i.e., heparin-DOCA) was dialyzed for 1 day against water using a membrane (MWCO 3,500), and then heparin-DOCA was freeze dried.

The synthesized heparin-DOCA was further purified by reverse phase chromatography.

A phenyl-Sepharose CL-4B column (HR 16/30 I.D.) was washed with 100 ml of distilled water, 40 ml of 50 mM phosphate buffer (pH 7.0), 40 ml of 50 mM phosphate buffer (pH 7.0) containing 1.7 M ammonium sulfate, and 40 ml of 50 mM phosphate buffer, respectively. Five milliliters of the heparin-DOCA solution (1 mg/ml) was loaded in the column and the heparin-DOCA was fractionated by step elution with an ammonium sulfate solution. Elution was carried out with phosphate buffer for 20 minutes, followed by the ammonium sulfate solution (50 mM phosphate buffer (pH 7.0)+1.7 M ammonium sulfate) with the flow rate of 1 ml/min. Heparin-DOCA was eluted in the ammonium sulfate solution. The purified heparin-DOCA solution was dialyzed in distilled water and lyophilized.

The heparin derivatives prepared according to this procedure were characterized by FT-IR and NMR according to methods well known in the art to prove the successful coupling between heparin and the hydrophobic agent. Y. Lee, H. T. Moon & Y. Byun, Preparation of Slightly Hydrophobic Heparin Derivatives Which Can Be Used for Solvent Casting in Polymeric Formulation, 92 Thromb. Res. 149–156 (1998).

EXAMPLE 2

Preparation of Heparin-Cholesterol Conjugates. The hydroxyl group of cholesterol was activated by reaction with chloroacetic acid to result in a free carboxyl group. This modified cholesterol was then reacted with HOSu and DCC in 10 ml of DMF according to the procedure of Example 1. The mole ratio of cholesterol, HOSu, and DCC was 1:1.6:1.6 and reaction was for 5 hours at room temperature. To remove the unreacted DCC and HOSu, water was added and the solution was filtered with a 0.45 µm membrane. Next, the activated cholesterol was reacted with heparin solution for 4 hours. Two products, a water-soluble product and a water-insoluble product, were obtained from the reaction. These products were treated according to the procedure described above in Example 1.

EXAMPLE 3

Synthesis of Heparin-Alkanoic Acid Conjugates. Lauric acid and palmitic acid were coupled to heparin according to the procedure of Example 1. The carboxyl group of the alkanoic acids were coupled with amine groups of heparin to form amide bonds. Coupling agents were also HOSu and DCC.

EXAMPLE 4

Synthesis of Heparin-Cholic Acid Conjugates. In this example, the procedure of Example 1 is followed except that cholic acid is substituted for DOCA.

EXAMPLE 5

Synthesis of Heparin-Chenodeoxycholic Acid Conjugates. In this example, the procedure of Example 1 is followed except that chenodeoxycholic acid is substituted for DOCA.

EXAMPLE 6

Synthesis of Heparin-Ergosterol Conjugates. In this example, the procedure of Example 2 is followed except that ergosterol is substituted for cholesterol.

EXAMPLE 7

Synthesis of Insulin-DOCA Conjugates. In this example, the procedure of Example 1 is followed except that insulin is substituted for heparin. The amine groups of insulin, i.e., GlyA1, PheB1, and LysB29, are coupled with carboxyl groups of DOCA.

EXAMPLE 8

Synthesis of Calcitonin-DOCA Conjugates. In this example, the procedure of Example 1 is followed except that calcitonin is substituted for heparin. An amine group of calcitonin is coupled to a carboxyl group of DOCA.

EXAMPLE 9

Measurement of Bioactivity of Heparin Derivatives. For heparin-DOCA, heparin-cholesterol and heparin-alkanoic acid prepared according to the procedures of Examples 1–3, the production yield, molecular weight, and binding mole ratios between heparin and hydrophobic agents varied according to the mole ratio of reactants. The yield of heparin-DOCA conjugates was in the range of 71 to 77%. The amount of hydrophobic agent in modified heparin derivatives was calculated by subtracting the molecular weight of heparin (i.e., 12,386 daltons as determined by light scattering) from the measured molecular weight of each heparin derivative. As the feed mole ratio of deoxycholic acid to heparin was increased from 1:6 to 1:200, the amount of DOCA in heparin-DOCA conjugates was increased from 7 to 24%. For the heparin-cholesterol conjugates, the yield also was in the range from 73 to 78%. The amount of cholesterol in such hydrophobic heparin conjugates, however, was slightly lower than the amount of DOCA in heparin-DOCA conjugates. In heparin-lauric acid and heparin-palmitic acid conjugates, similar amounts of alkanoic acid were coupled to heparin.

Anticoagulant activities of heparin derivatives were determined by aPTT assay and FXa chromogenic assay. The activities of heparin derivatives in the prevention of fibrin clot formation were measured by aPTT assay. Each of the platelet-poor-plasma containing heparin standards (0.1 to 0.7 U/ml, 0.1 ml) and plasma samples containing heparin derivatives (0.1 ml) was incubated with 0.1 ml of aPTT reagent for 2 min at 37° C. After the incubation, 0.1 ml of 0.02 M calcium chloride was added, and the time was recorded from this point until the fibrin clot was formed. The bioactivity of the heparin derivative was calculated by comparing the clotting time with the heparin standard curve. The clotting time was linearly proportional to the activity of heparin in the plasma.

The activity and the concentration of heparin derivatives were also determined by FXa chromogenic assay. Each of the heparin standards and plasma samples containing heparin derivatives (25 µl) was mixed with 200 µl of AT III solution (0.1 IU/ml), where the ATIII concentration was in excess of the heparin concentration. This solution was incubated at 37 for 2 min, and 200 µl of FXa (4 nkcat/ml) was added. The resulting solution was then incubated for an additional 1 min. The concentration of FXa was also in excess of the heparin concentration. FXa substrate (200 µl, 0.8 µmol/ml) was then added and incubated at 37 for 5 min. The reaction was terminated by adding 200 µl of acetic acid (50% solution). The bioactivity and the concentration of heparin in the plasma sample were calculated from the absorbance at 405 nm. These data are summarized in Table 1.

TABLE 1

| Compound | Mole ratio[a] | Bioactivity (IU/mg) | Mol. Wt. |
|---|---|---|---|
| Heparin | — | 140 | 12,386 |
| Heparin-DOCA | 2.5 | 130 ± 1.0 | 13,357 |
| Heparin-DOCA | 5 | 113 ± 2.8 | 14,403 |
| Heparin-DOCA | 10 | 100 ± 4.3 | 16,320 |
| Heparin-cholesterol | 4.5 | 122 ± 6.7 | 13,791 |
| Heparin-lauric acid | 5 | 118 ± 5.0 | 13,400 |
| Heparin-palmitic acid | 4.4 | 123 ± 2.7 | 13,500 |

[a]Mole ratio of hydrophobic agent to heparin.

EXAMPLE 10

Oral Administration of Heparin-DOCA. Sprague-Dawley rats (male, 250–260 g) were fasted for 12 hours before dosing. The rats were anesthetized with diethyl ether and then were administered a single dose of heparin derivative through an oral gavage that was carefully passed down the esophagus into the stomach. The gavage was made of stainless steel with a blunt end to avoid causing lesions on the tissue surface. The solution containing the heparin derivative was prepared in a sodium bicarbonate buffer (pH 7.4). The total administered volume of heparin-derivative-containing solution was 0.3 ml. The dose amount was varied at 50, 80, 100, and 200 mg/kg, respectively. There were 9 rats in each group. Blood (450 µl) was collected serially by capillary from the retro-orbital plexus at each time point and directly mixed with 50 µl of sodium citrate (3.8% solution). The blood samples were immediately centrifuged at 2500×g and 4° C. for 5 minutes. The clotting time and the concentration of heparin derivative in the plasma were measured by aPTT assay and FXa assay, respectively.

The absorption of heparin-DOCA in the GI tract was determined according to the dose amount in the range of 50 to 200 mg/kg. In this experiment, the mole ratio of coupled DOCA to heparin in the heparin-DOCA conjugate was 10. When raw heparin was administered orally to rats, the clotting time, measured by aPTT assay, was about 18 seconds and this value did not change over time. The average value of the baseline was 18 seconds, indicating that the raw heparin was not absorbed in the GI tract. When the physical mixture or admixture of heparin and DOCA was administered orally, the aPTT value was about 20 seconds, and this value did not change over time. On the other hand, when heparin-DOCA conjugate was orally administered, the clotting time increased as shown in FIG. 1. Since the blood sampling was carried out at one-hour intervals and the maximum clotting time was shown at the one-hour time point, the real maximum clotting time could not be determined. However, the clotting time at one hour was linearly increased with the increase of dosage. When heparin-DOCA conjugate was given at 50, 80, 100, and 200 mg/kg, the clotting times at one hour were 25.8±2.6, 43.1±4.0, 51.2±9.3, and 136±33 seconds, respectively. When heparin-DOCA conjugate was administered at 200 mg/kg, the clotting time at one hour increased greatly, above 7-times the baseline. Since the therapeutic window of heparin is 1.5 to 2.5 times the baseline, the therapeutic effect can be seen at an 80–100 mg/kg dose. Therefore, the heparin-DOCA conjugate greatly enhanced the absorption of heparin in the GI tract, in contrast to DOCA mixed with heparin in a physical mixture, which did not enhance heparin absorption.

Figure 2:
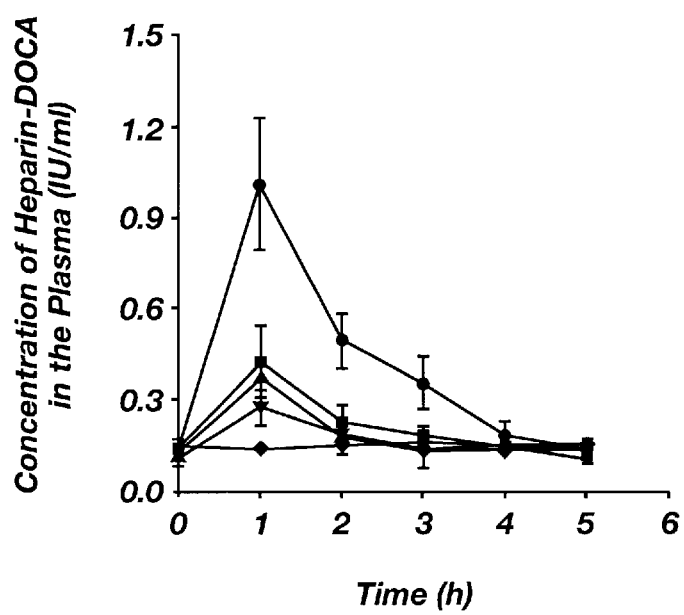
FIG. 2 shows concentration profiles as measured by FXa assay of heparin-DOCA conjugate after oral administration in rats: ♦—100 mg/kg raw heparin (control), ▼—50 mg/kg heparin-DOCA conjugate, ▲—80 mg/kg heparin-DOCA conjugate, ■—100 mg/kg heparin-DOCA conjugate, and ●—200 mg/kg heparin-DOCA conjugate; data are plotted as mean±SD, n=9.

The concentration of heparin-DOCA conjugate in the plasma was determined by FXa assay, as shown in FIG. 2. The concentration profiles of heparin-DOCA conjugate over time were similar to the results of the aPTT assay shown in FIG. 1. The concentration of absorbed heparin-DOCA increased with the increase of the dosage. The therapeutic target range was 0.1 to 0.2 IU/ml. For a 200 mg/kg does of heparin-DOCA conjugate, the mean concentration peak at one hour was about 9–10 times the baseline and the concentration at that time was about 1.0 IU/ml. The plasma concentration of heparin-DOCA conjugate returned to the baseline after 3 hours. Therefore, the absorption of heparin-DOCA in the GI tract was confirmed.

EXAMPLE 11

Heparin-DOCA Conjugate Absorption in the GI Tract of Rats. To determine the absorption of heparin-DOCA conjugate in the GI tract as a function of the ratio of DOCA to heparin, heparin-DOCA conjugates were synthesized with DOCA:heparin mole ratios of 2.5, 5.0, and 10.0, as described in Example 1. As shown in Table 1, the bioactivity of heparin-DOCA conjugates decreased slightly as the mole ratio of DOCA to heparin increased. However, since the molecular weight of heparin-DOCA increased as the mole ratio of DOCA to heparin increased, the bioactivity of heparin-DOCA conjugates as a function of mole ratio decreased only about 5%. That is, the bioactivities of heparin and heparin-DOCA conjugate (10:1 mole ratio) were 1,734 and 1,632±7 IU/mol, respectively.

Figure 3:
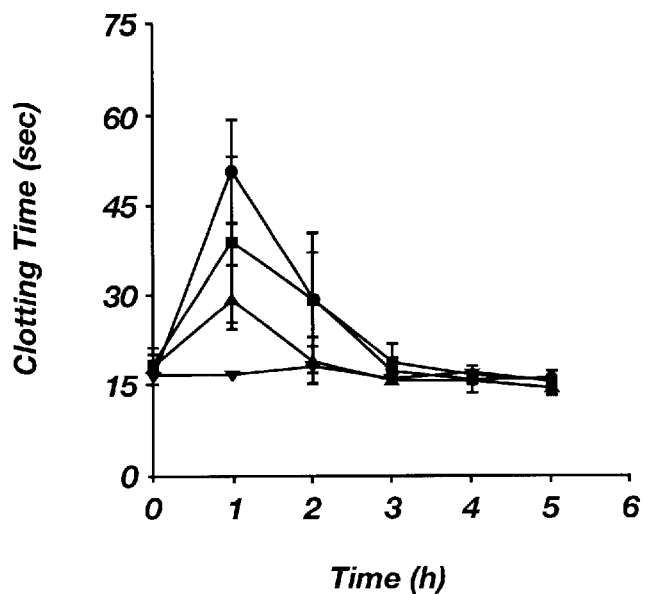
FIG. 3 shows clotting time profiles in rats of heparin-DOCA conjugates as a function of the mole ratio of DOCA to heparin: ▼—raw heparin, ▲—2.5 mole ratio, ■—5.0 mole ratio, and ●—10.0 mole ratio; data are plotted as mean±SD, n=9.

FIG. 3 shows the change in the clotting time according to the coupled mole ratio of DOCA to heparin. In this experiment, the dosage of heparin-DOCA conjugate was 100 mg/kg. When the mole ratio of the coupled DOCA to heparin increased, the bioactivity of heparin-DOCA conjugate slightly decreased, as shown in Table 1, whereas the maximum clotting time increased. This result indicates that the heparin-DOCA conjugate facilitated absorption of heparin in the GI tract of rats.

EXAMPLE 12

Figure 4:
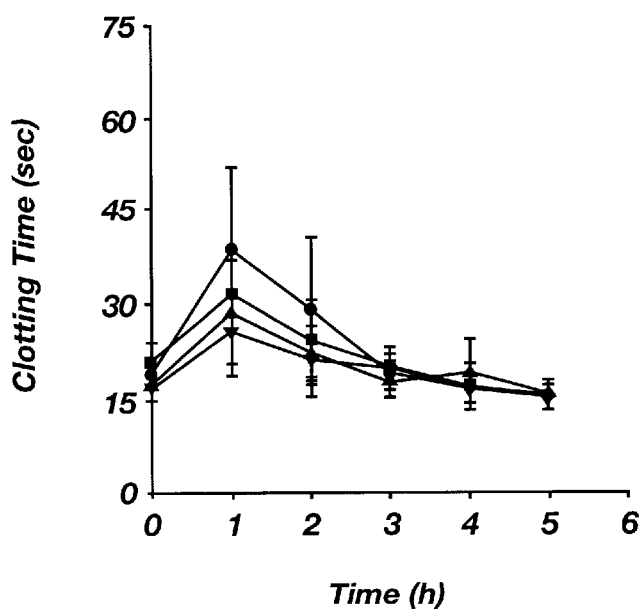
FIG. 4 shows clotting time profiles in rats of heparin derivatives as a function of the hydrophobic agent conjugate to heparin: ▼—heparin-lauric acid conjugate, ▲—heparin-palmitic acid conjugate, ■—heparin-cholesterol conjugate, and ●—heparin-DOCA conjugate; data are plotted as mean±SD, n=9.

Effect of Hydrophobic Agent Coupled to Heparin on GI Absorption in Rats. To show the effect of a hydrophobic agent coupled to heparin on GI absorption, heparin-DOCA, heparin-cholesterol, heparin-palmitic acid, and heparin-lauric acid prepared according to Examples 1–3 were tested. As shown in Table 1, the mole ratio of hydrophobic agent to heparin was controlled in the range of 4 to 4.5. The bioactivities of these heparin derivatives were similar to each other, i.e., in the rage of 113 to 123 IU/mg. FIG. 4 shows the absorption values obtained after oral administration of 100 mg/kg of these heparin derivatives. Maximum clotting times at one hour after administration, as measured by the aPTT assay, were 32±6.1 seconds for heparin-cholesterol, 29±8.3 seconds for heparin-palmitic acid, and 25.9±6.6 seconds for heparin-lauric acid. The carbon numbers of cholesterol, palmitic acid, and lauric acid were 24, 16, and 12, respectively, and the hydrophobicity of the hydrophobic agent is proportion to the number of carbon atoms. Thus, the maximum clotting time increase with the hydrophobicity of the coupled hydrophobic agent. This result indicated that the hydrophobicity of the heparin derivative was an important property for increasing the absorption of heparin in the GI tract. Even though cholesterol is more hydrophobic than DOCA, however, heparin-DOCA conjugate exhibited a higher clotting time than heparin-cholesterol conjugate. Possible explanations for this observation include (1) the amphiphilic properties of heparin-DOCA conjugate, which may improve the permeability of the heparin derivative in the GI wall, and (2) the interaction between the DOCA moiety of the heparin-DOCA conjugate and the DOCA receptors in the GI wall, especially in the ileum, which might increase the adhesion of heparin-DOCA conjugate to the GI wall, thereby increasing the probability of absorption.

EXAMPLE 13

Histological Evaluation of GI Tract. In this example heparin-DOCA conjugate was administered to rats by oral gavage according to the procedure of Example 10. The mole ratio of coupled DOCA to heparin in the heparin-DOCA conjugate was 10. That is, ten molecules of DOCA were coupled to one molecule of heparin. The dose amount was 200 mg/kg. At 1, 2, and 3 hours after dosing, rats were anesthetized with diethyl ether and were sacrificed by cutting the diaphragm. Gastric, duodenal, jejunal, and ileal tissues were removed from the rats and fixed in neutral buffered formalin for processing. GI tissues sampled before administration of heparin-DOCA conjugate were prepared as control samples. The tissue specimens were washed with alcohol to remove any water. Specimens were perfused with colored silicone and embedded in paraffin. The embedded specimens were cut into 5 μm sections using a microtome at −20° C., and picked up on a glass slide. The tissue sections were then washed with xylene and absolute alcohol, respectively, to remove the paraffin. The prepared 5 μm sections were then stained with hematoxylin and eosin (H&E) according to procedures well known in the art. At least 4 rats were used for each treatment.

For evaluation by transmission electron microscopy (TEM), the gastric, duodenal, jejunal, and ileal tissues were fixed with 1% osmium tetroxide in PBS (0.1 M, pH 7.4), and then hydrated by changing the alcohol concentration gradually from 50 to 100%. The hydrated tissues were infiltrated with propylene oxide and embedded with an epon mixture. The embedded tissues were sectioned as about 50–60 nm thickness slides. These slides were stained very lightly with uranyl acetate and lead citrate for 1 minute, and were observed by TEM (Hitachi 7100, Tokyo, Japan).

Figure 5A:
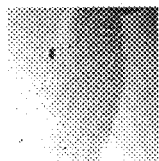
FIGS. 5A–P show micrographs of hematoxylin and eosin stained gastrointestinal tissues that were isolated from rats after oral administration of 100 mg/kg of heparin-DOCA conjugate.
Figure 5B:
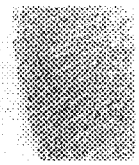
Figure 5C:
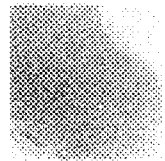
Figure 5D:
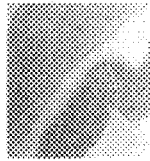
Figure 5E:
FIGS. 5E–H show cross sections of the duodenum after 0, 1, 2, and 3 hours, respectively.
Figure 5F:
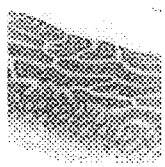
Figure 5G:
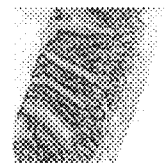
Figure 5H:
Figure 5I:
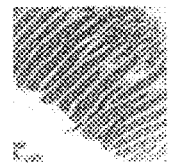
FIGS. 5I–L show cross sections of the jejunum after 0, 1, 2, and 3 hours, respectively.
Figure 5J:
Figure 5K:
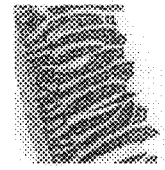
Figure 5L:
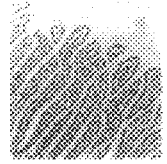
Figure 5M:
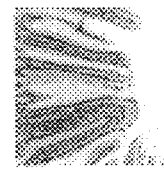
Figure 5N:
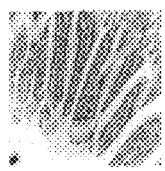
Figure 5O:
Figure 5P:
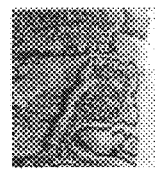

FIGS. 5A–P show that there was no evidence of damage to the GI wall, such as occasional epithelial cell shedding, villi fusion, congestion of mucosal capillary with blood, or focal trauma, in any parts of the stomach, duodenum, jejunum, or ileum. These results confirm that increased absorption of heparin derivatives was not caused by the disruption of the gastrointestinal epithelium.

FIGS. 6A–P show the electron microscopic morphology of microvilli after exposure to heparin derivatives. The control samples showed healthy tight junctions, microvilli, and mitochondria. After 1, 2, and 3 hours, the cell appearance in all sections showed no signs of damage, such as microvilli fusion, dissolution, disoriented cell layer with porosity, or cytotoxic effect. Microvilli exposed to heparin derivatives were also found to be as healthy as the control. The absence of tissue damage indicates that the enhancing effect of the coupled DOCA on heparin absorption in the GI tract was not caused by changing the tissue structure.

EXAMPLE 14

Conjugation of Lower Molecular Weight Heparin to DOCA. Conjugates of heparin to DOCA were synthesized according to the procedure of Example 1 except that unfractionated heparin ("UFH"), i.e., the compound referred to simply as "heparin" in previous examples, 6000 molecular weight heparin ("LMWH(6K)"), and 3000 molecular weight heparin ("LMWH(3K)") were used. The resulting conjugates, UFH-DOCA, LMWH(6K)-DOCA, and LMWH (3K)-DOCA, were then characterized, as shown in Table 2.

TABLE 2

| Conjugate | Molecular Weight[a] | Absolute Activity (IU/mg) by aPTT | Absolute Activity (IU/mg) by FXa | Mole Ratio of DOCA to Heparin |
|---|---|---|---|---|
| LMWH(3K) | 2,910 | 50.8 ± 4.9 | 124.7 ± 0.8 | N/A |
| LMWH(3K)-DOCA | 3,410 | 40.0 ± 7.7 | 121.5 ± 1.6 | 1.3 |
| LMWH(6K) | 6,150 | 127.1 ± 2.4 | 148.4 ± 0.2 | N/A |
| LMWH(6K)-DOCA | 7,576 | 108.5 ± 4.9 | 134.3 ± 0.8 | 3.6 |
| UFH | 12,386 | 184 | 167 | N/A |
| UFH-DOCA | 16,320 | 128.8 ± 2.3 | 116.9 ± 0.5 | 10 |

[a]Measured by light scattering.

The maximum ratio of DOCA to heparin obtained in UFH-DOCA was 10 when the feed ratio of UFH to DOCA was 1:200. Under these conditions, the ratios obtained with lower molecular weight heparins were 1.3 for LMWH(3K)-DOCA and 3.6 for LMWH(6K)-DOCA. The mole ratio of DOCA to heparin decreased with the decrease in molecular weight of heparin because of the fewer number of amine groups available for bonding to DOCA. Bioactivities of the heparin-DOCA conjugates also decreased with the decrease of molecular weight of heparin, although all heparin-DOCA conjugates demonstrated similar bioactivities in the range of 116.9±1.6 to 134.3±0.8 by FXa assay. After conjugation with DOCA, all of the heparin-DOCA conjugates showed above 70% relative bioactivity compared to the unmodified heparin.

EXAMPLE 15

Figure 7A:
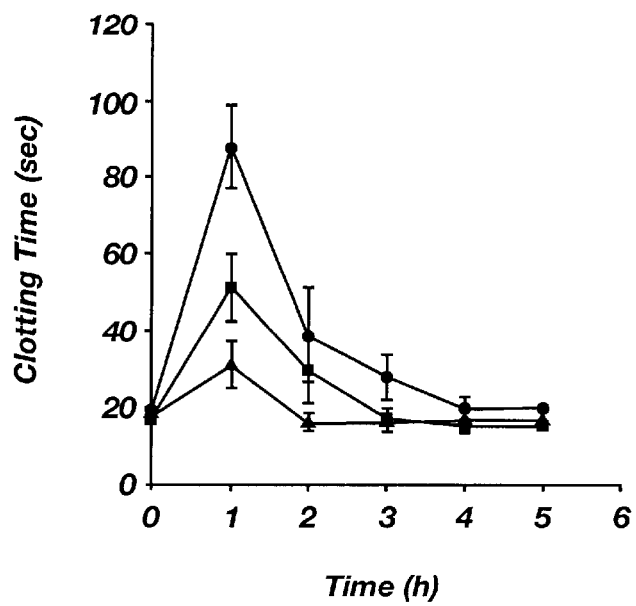
FIGS. 7A and 7B show clotting time profiles (FIG. 7A) and concentration profiles (FIG. 7B) of heparin-DOCA conjugates after oral administration in rats: ▲—LMWH (3K)-DOCA; ●—LMWH(6K)-DOCA; ■—heparin-DOCA (also referred to herein as UFH-DOCA).
Figure 7B:
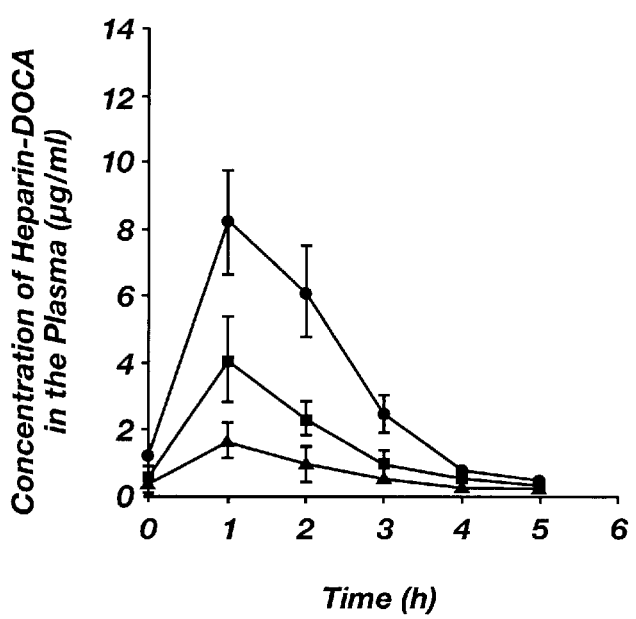

Oral Absorption of Lower Molecular Weight Heparin-DOCA Conjugates. The lower molecular weight heparin-DOCA conjugates prepared in Example 14 were tested for absorption in the GI tract of rats after oral administration according to the procedure of Example 10. FIG. 7 shows the effect of molecular weight of heparin on the absorption of heparin-DOCA conjugates in the GI tract. LMWH(3K)-DOCA, LMWH(6K)-DOCA, and UFH-DOCA (i.e., heparin-DOCA) were each administered by oral gavage at 100 mg/kg dosage. The clotting times of LMWH(3K)-DOCA and UFH-DOCA were lower than that of LMWH (6K)-DOCA; the mean aPTT times at 1 hour were 31.0±6.01 and 51.0±8.7, respectively (p<0.005). The suggest that the clotting time of LMWH(6K)-DOCA was 1.5- and 3-fold greater than those of LMWH(3K)-DOCA and UFH-DOCA, respectively. The concentration profiles of heparin-DOCA conjugates with time were similar to the results of the aPTT assay. When UFH-DOCA was administered at 100 mg/kg dosage, the peak concentrations of plasma was 4.10±1.3 µg/ml, which was very low compared to the concentration of LMWH(6K)-DOCA at the same dosage level.

Figure 8A:
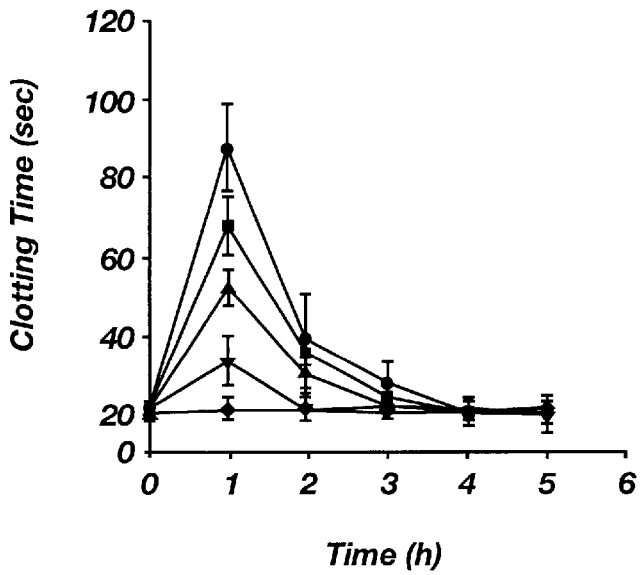
FIGS. 8A and 8B show clotting time profiles (FIG. 8A) and concentration profiles (FIG. 8B) of LMWH(6K)-DOCA after oral administration in rats: ♦—20 mg/kg of LMWH (6K) control; ▼—100 mg/kg of LMWH(6K) control; ▲—20 mg/kg LMWH(6K)-DOCA; ■—50 mg/kg LMWH (6K)-DOCA; ●—100 mg/kg LMWH(6K)-DOCA.

The absorption of LMWH(6K)-DOCA in the GI tract was determined according to the dose amount in the range of 20 to 100 mg/kg, as shown in FIG. 8. When 100 mg/kg of LMWH(6K) was administered orally to rats, the clotting time as measured by aPTT assay was about 30 seconds at 1 hour after dosing. This curve fell to baseline at 2 hours after dosing. On the other hand, oral delivery of LMWH(6K)-DOCA resulted in the increased heparin absorption in rats as shown by the highly elevated aPTT values. When LMWH (6K)-DOCA was dosed at 100 mg/kg, the peak plasma aPTT value was about 87.8±11.1 seconds (the baseline aPTT values averaged 20 seconds). Heparin derivatives dosed at 20 mg/kg and 50 mg/kg gave mean peak aPTT responses of 52.5±4.7 and 68.4±7.2 seconds, respectively (p<0.005). The therapeutic range of heparin, which is about 1.5–2.5 times baseline in aPTT, is matched with a dose of 20 mg/kg, as shown in FIG. 8A.

Figure 8B:
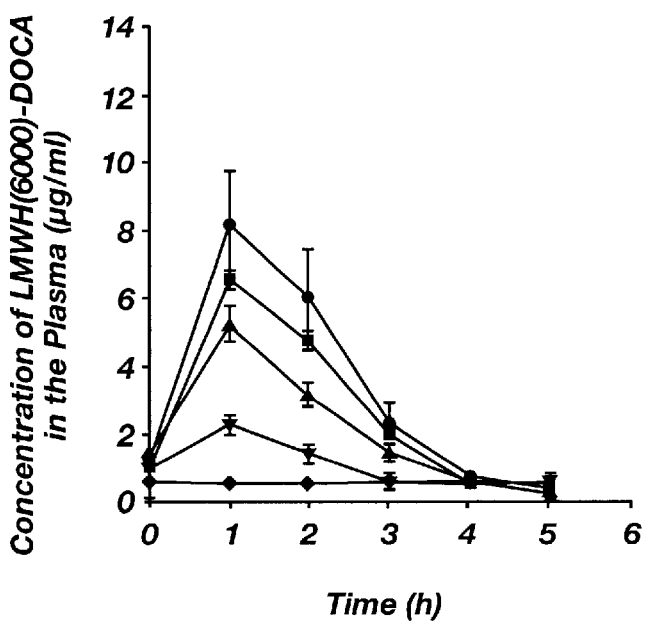

Concentrations of heparin derivatives in the plasma could be determined using the anti-FXa assay. When 100 mg/kg of LMWH(6K)-DOCA was administered orally, the concentration of LMWH(6K) was 1.34±0.28 µg/ml. The low concentration of LMWH(6K) in the plasma could not facilitate anticoagulation activity. However, the maximum peak of LMWH(6K)-DOCA was 8.21±1.6 µg/ml at a dose of 100 mg/kg, as shown in FIG. 8B. The therapeutic target range was 0.1 to 0.2 IU/ml. The mean concentration peaks were about 9–10 times the baseline. These results suggest that heparin derivatives can perform as an oral anticoagulant drug for patients at risk for deep vein thrombosis and pulmonary embolism.

EXAMPLE 16

Histological Evaluation of the GI Tract after Oral Administration of Lower Molecular Weight Heparin-DOCA Conjugates. GI tract tissues from rats given a single dose of 100 mg/kg of lower molecular weight heparin-DOCA conjugates prepared according to the procedure of Example 14 were examined histologically according to the procedures of Example 13. The results were substantially similar to those of Example 13. That is, no evidence of damage to any of the tissues of the GI wall were detected.

What is claimed is:

1. A method of treating a patient in need of anticoagulation therapy comprising orally administering an effective amount of a composition comprising heparin covalently bonded to a hydrophobic agent selected from the group consisting of bile acids, sterols, and alkanoic acids, and mixtures thereof.

2. The method of claim 1 wherein said hydrophobic agent is a bile acid selected from the group consisting of cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and mixtures thereof.

3. The method of claim 2 wherein said bile acid is deoxycholic acid.

4. The method of claim 1 wherein said hydrophobic agent is a sterol selected from the group consisting of cholestanol, coprostanol, cholesterol, epicholesterol, ergosterol, ergocalciferol, and mixtures thereof.

5. The method of claim 1 wherein said hydrophobic agent is an alkanoic acid comprising about 4 to 20 carbon atoms.

6. The method of claim 5 wherein said alkanoic acid is a member selected from the group consisting of butyric acid, valeric acid, caproic acid, caprylic acid, capric acid, lauric acid, myristic acid, palmitic acid, stearic acid, and mixtures thereof.

7. The method of claim 1 wherein said composition further comprises a pharmaceutically acceptable carrier.

8. The method of claim 1 wherein said heparin comprises a molecular weight of at least about 3000.

9. The method of claim 8 wherein said heparin comprises a molecular weight of at least about 6000.

10. The method of claim 1 wherein said heparin comprises a molecular weight less than about 12,000.

11. A method for enhancing oral administration of a macromolecular agent comprising:

(a) conjugating said macromolecular agent to a hydrophobic agent selected from the group consisting of bile acids, sterols, alkanoic acids, and mixtures thereof to result in a hydrophobized macromolecular agent; and (b) orally administering an effective amount of said hydrophobized macromolecular agent to a patient in need thereof.

12. The method of claim 11 wherein said hydrophobic agent is a bile acid selected from the group consisting of cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and mixtures thereof.

13. The method of claim 12 wherein said bile acid is deoxycholic acid.

14. The method of claim 11 wherein said hydrophobic agent is a sterol selected from the group consisting of cholestanol, coprostanol, cholesterol, epicholesterol, ergosterol, ergocalciferol, and mixtures thereof.

15. The method of claim 11 wherein said hydrophobic agent is an alkanoic acid comprising about 4 to 20 carbon atoms.

16. The method of claim 15 wherein said alkanoic acid is a member selected from the group consisting of butyric acid, valeric acid, caproic acid, caprylic acid, capric acid, lauric acid, myristic acid, palmitic acid, stearic acid, and mixtures thereof.

17. The method of claim 11 wherein said macromolecular agent is a member selected from the group consisting of heparin, heparan sulfate, sulfonyl polysaccharide, polysaccharide derivatives, and mixtures thereof.

18. The method of claim 17 wherein said macromolecular agent is heparin.

19. The method of claim 11 wherein said macromolecular agent is a peptide.

20. The method of claim 19 wherein said macromolecular agent is insulin.

21. The method of claim 19 wherein said macromolecular agent is calcitonin.

22. A method of treating a patient in need of anticoagulation therapy comprising orally administering an effective amount of a composition comprising a member selected from the group consisting of heparin, heparan sulfate, sulfonyl polysaccharide, heparinoids, and mixtures thereof covalently bonded to a hydrophobic agent selected from the group consisting of bile acids, sterols, and alkanoic acids, and mixtures thereof.

* * * * *